United States Patent [19]

Bagli et al.

[11] 4,258,188

[45] Mar. 24, 1981

[54] 2-(1-PIPERAZINYL)-CYCLOHEP-TIMIDAZOLE DERIVATIVES

[75] Inventors: Jehan F. Bagli, Kirkland; Tibor Bogri, Montreal, both of Canada

[73] Assignee: American Home Products Corporation, New York, N.Y.

[21] Appl. No.: 118,343

[22] Filed: Feb. 4, 1980

[51] Int. Cl.$^3$ ............... C07D 401/14; C07D 403/04; A61K 31/495

[52] U.S. Cl. ................... 544/364; 544/139; 544/370; 544/382; 424/250

[58] Field of Search ................. 544/364, 370

[56] References Cited

U.S. PATENT DOCUMENTS

| | | | |
|---|---|---|---|
| 3,461,131 | 8/1969 | Sunagawa et al. | 548/302 |
| 3,849,431 | 11/1974 | Gallay et al. | 544/370 |
| 4,093,726 | 6/1978 | Winn et al. | 544/370 |

*Primary Examiner*—Donald G. Daus
*Assistant Examiner*—James H. Turnipseed
*Attorney, Agent, or Firm*—Arthur E. Wilfond

[57] ABSTRACT

2-(1-Piperazinyl)-cycloheptimidazole derivatives are disclosed. The foregoing compounds are useful antihypertensive agents.

33 Claims, No Drawings

2-(1-PIPERAZINYL)-CYCLOHEPTIMIDAZOLE DERIVATIVES

BACKGROUND OF THE INVENTION

This invention relates to novel 2-(1-piperazinyl)-cycloheptimidazole derivatives, to a process for their preparation and to therapeutically acceptable acid addition salts and pharmaceutical compositions of the derivatives. These derivatives are useful for treating hypertension in mammals.

Illustrative of references obtainable from a literature search for cycloheptimidazole derivatives is U.S. Pat. No. 3,461,131 to G. Sunagawa et al., Aug. 12, 1969. Of the cycloheptimidazole derivatives, the 2-(substituted amino)-cycloheptimidazole derivatives exemplified by U.S. Pat. No. 3,461,131, cited above, can be considered most closely related to the compounds of this invention. However, the compounds of this invention have a piperazinyl ring instead of the amino group at position 2 of the cycloheptimidazole ring system of said patent.

SUMMARY OF THE INVENTION

The compounds of this invention are represented by formula I

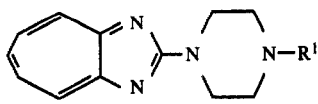
(I)

in which $R^1$ is hydrogen, lower alkyl, lower alkenyl, lower alkynyl, hydroxy(lower)-alkyl, lower alkoxycarbonyl, formyl, phenyl(lower)alkyl, phenylcarbonyl, 2- or 3-furanylcarbonyl, phenyl, 2- or 3-pyridinyl, 1-oxo(lower)alkoxy(lower)alkyl, 2-imidazolinyl, aminoiminomethyl, aminothioxomethyl, (lower alkylamino)thioxomethyl, (phenylamino)thioxomethyl, hydrazinothioxomethyl, (lower alkylthio)-thioxomethyl, sodium thiothioxomethyl, α-halophenyl, α-halophenyl-α-phenylmethyl or phenyl substituted with one or two members selected from the group consisting of halo, lower alkyl, lower alkoxy or trifluoromethyl.

A preferred class of compounds of formula I is one in which $R^1$ is hydrogen lower alkyl, lower alkenyl, lower alkynyl, hydroxy(lower)alkyl, lower alkoxycarbonyl, formyl, phenyl(lower)alkyl, phenylcarbonyl, 2-furanylcarbonyl, phenyl, 2-pyridinyl, 1-oxo(lower)alkoxy(lower)alkyl, 2-imidazolinyl, aminoiminomethyl, aminothioxomethyl, (lower alkylamino)thioxomethyl, (phenylamino)thioxomethyl, hydrazinothioxomethyl, (lower alkylthio)thioxomethyl, sodium thiothioxomethyl, α-halophenyl-α-phenylmethyl or phenyl substituted with one member selected from the group consisting of halo, lower alkyl, lower alkoxy or trifluoromethyl.

Still another preferred class of compounds of formula I is one in which $R^1$ is hydrogen, lower alkyl, lower alkenyl, lower alkynyl, hydroxy(lower)alkyl, lower alkoxycarbonyl, formyl, 2-furanylcarbonyl, 1-oxo(lower)alkoxy(lower)alkyl, aminoiminomethyl, hydrazinothioxomethyl or sodium thiothioxomethyl.

The therapeutically acceptable acid addition salts of the compounds of formula I also are included within the scope of this invention.

The compounds of formula I can form a pharmaceutical composition comprising a compound of formula I, or a therapeutically acceptable acid addition salt thereof, and a pharmaceutically acceptable carrier.

The compounds of this invention can be used to treat hypertension in a hypertensive mammal by administering to the mammal an effective antihypertensive amount of a compound of formula I or a therapeutically acceptable acid addition salt thereof.

DETAILED DESCRIPTION OF THE INVENTION

The term "lower alkyl" as used herein means straight chain alkyl radicals containing from one to six carbon atoms and branched chain alkyl radicals containing three or four carbon atoms and includes methyl, ethyl, propyl, 1-methylethyl, butyl, 2-methylpropyl, pentyl, hexyl and the like, unless stated otherwise.

The term "lower alkoxy" as used herein means straight chain alkoxy radicals containing from one to six carbon atoms and branched chain alkoxy radicals containing three or four carbon atoms and includes methoxy, ethoxy, 1-methylethoxy, butoxy, hexoxy and the like.

The term "1-oxo(lower)alkoxy" as used herein means straight chain 1-oxoalkoxy radicals containing from two to six carbon atoms and branched chain 1-oxoalkoxy radicals containing four to six carbon atoms and includes acetyloxy, 1-oxopropoxy, 1-oxobutoxy, 2,2-dimethyl-1-oxopropoxy, 1-oxohexoxy and the like.

The term "lower alkynyl" as used herein means straight chain alkynyl radicals containing from two to six carbon atoms and branched chain alkynyl radicals containing four carbon atoms and includes ethynyl, 2-propynyl, 1-methyl-2-propynyl, 3-hexynyl and the like.

The term "lower alkenyl" as used herein means straight chain alkenyl radicals containing from two to six carbon atoms and branched chain alkenyl radicals containing three or four carbon atoms and includes ethenyl, 2-methyl-2-propenyl, 4-hexenyl and the like.

The term "lower alkanol" as used herein means both straight and branched chain alkanols containing from one to four carbon atoms and includes methanol, ethanol, isopropanol, butanol and the like.

The term "halo" as used herein means halogens and includes fluorine, chlorine, bromine and iodine, unless stated otherwise.

The term "organic proton acceptor" as used herein means the organic bases, or amines for instance, triethylamine, pyridine, N-ethyl-morpholine, 1,5-diazabicyclo[4.3.0]non-5-ene and the like.

The term "inorganic proton acceptor" as used herein means the inorganic bases, preferably the alkali metal hydroxides, carbonates and bicarbonates, for example, sodium hydroxide, potassium hydroxide, sodium carbonate, sodium bicarbonate, potassium carbonate and the like.

The term "proton acceptor" as used herein means a proton acceptor selected from an organic proton acceptor and inorganic proton acceptor, as defined herein.

The compounds of formula I are capable of forming acid addition salts with therapeutically acceptable acids. The acid addition salts are prepared by reacting the base form of the appropriate compound of formula I with one or more equivalents, preferably with an excess, of the appropriate acid in an organic solvent, for example, diethyl ether or an ethanol-diethyl ether mixture. These salts, when administered to a mammal, possess the same pharmacologic activities as the corresponding bases. For many purposes it is preferable to administer the salts rather than the base compounds. Examples of suitable acids to form these salts include: the common mineral acids, e.g., hydrohalic, sulfuric or phosphoric acids; the organic acids, e.g., formic, acetic, maleic, malic, citric, or tartaric acid; and acids which are sparingly soluble in body fluids and which impart slow-release properties to their respective salts, e.g., pamoic acid, tannic acid or carboxymethyl cellulose. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

The antihypertensive effect of the compounds of formula I or therapeutically acceptable acid addition salts thereof is demonstrated in standard pharmacological tests, for example, in tests conducted in the spontaneously hypertensive rat (SHR) using the testing method described by I. Varva, et al., Can. J. Physiol. Pharmacol., 51, 727 (1973). The latter test method is modified so that the test compound is administered orally to the rat by gastric gavage and the blood pressure is measured by the tail-cuff method before administration of the compound and up to 4 hours thereafter. Using this method, the following representative compounds of formula I are effective for reducing the blood pressure (BP) in the spontaneously hypertensive rat (the amount of test compound and its reduction in BP are indicated in the parentheses): 4-(2-cycloheptimidazolyl)piperazine-1-carboxylic acid ethyl ester (described in Example 1, at a dose of 1.0 mg/kg of body weight causes a 20% decrease in mean BP at 30 minutes), 2-(1-piperazinyl)cycloheptimidazole hydrochloride (described in Example 2, at a dose of 25 mg/kg of body weight causes a 14% decrease in mean BP at 4 hours), 4-(2-cycloheptimidazolyl)-1-piperazinecarboximidamide hydroiodide trihydrate (described in Example 3, at a dose of 10 mg/kg of body weight causes a 19% decrease in mean BP at 1 hour), 4-(2-cycloheptimidazolyl)-piperazine-1-carboxylic acid 2-methylpropyl ester (described in Example 4, at a dose of 25 mg/kg of body weight causes a 15% decrease in mean BP at 1 hour), 2-[4-(2-propenyl)-1-piperazinyl]-cycloheptimidazole (described in Example 5, at a dose of 10 mg/kg of body weight causes a 18% decrease in mean BP at 1 hour), 2-[4-(2-propynyl)-1-piperazinyl]-cycloheptimidazole (described in Example 5, at a dose of 25 mg/kg of body weight causes a 13% decrease in mean BP at 1 hour), 4-(2-cycloheptimidazolyl)-piperazine-1-carbothioic acid, sodium salt (described in Example 6, at a dose of 25 mg/kg of body weight causes a 16% decrease in mean BP at 4 hours), 4-(2-cycloheptimidazolyl)-piperazine-1-carbothioic acid hydrazide (described in Example 8, at a dose of 5 mg/kg of body weight causes a 21% decrease in mean BP at 1 hour), 2-(4-methyl-1-piperazinyl)cycloheptimidazole hydrochloride (described in Example 13, at a dose of 25 mg/kg of body weight causes a 10% decrease in mean BP at 4 hours), 2-[4-(2-furanylcarbonyl)-1-piperazinyl]-cycloheptimidazole (described in Example 14, at a dose of 50 mg/kg of body weight causes a 19% decrease in systolic BP at 1.5 hours), 2-(4-formyl-1-piperazinyl)cycloheptimidazole (described in Example 14, at a dose of 10 mg/kg of body weight causes a 19% decrease in mean BP at 1 hour), 4-(2-cycloheptimidazolyl)-1-piperazineethanol (described in Example 15, at a dose of 10 mg/kg of body weight causes a 19% decrease in mean BP at 1 hour) and 2,2-dimethylpropanoic acid, 2-[4-(2-cycloheptimidazolyl)-1-piperazinyl]ethyl ester (described in Example 16, at a dose of 10 mg/kg of body weight causes a 16 to 25% decrease in mean BP at 1 hour).

The compounds of formula I of this invention are used alone or in combination with pharmacologically acceptable carriers, the proportion of which is determined by the solubility and chemical nature of the compound, chosen route of administration and standard biological practice. For example, they are administered orally in solid form, i.e. capsule or tablet. They can also be administered orally in the form of suspensions or solutions or they may be injected parenterally. For parenteral administration they can be used in the form of a sterile solution containing other solutes, for example, enough saline or glucose to make the solution isotonic.

The tablet compositions contain the active ingredient in admixture with non-toxic pharmaceutical excipients known to be suitable in the manufacture of tablets. Suitable pharmaceutical excipients are, for example, starch, milk sugar, certain types of clay and so forth. The tablets can be uncoated or they can be coated by known techniques so as to delay disintegration and absorption in the gastrointestinal tract and thereby provide a delayed and/or sustained action over a longer period.

The aqueous suspensions of the compounds of formula I contain the active ingredient in admixture with one or more non-toxic pharmaceutical excipients known to be suitable in the manufacture of aqueous suspensions. Suitable excipients are, for example, methylcellulose, sodium alginate, gum acacia, lecithin and so forth. The aqueous suspensions can also contain one or more preservatives, one or more coloring agents, one or more flavoring agents and one or more sweetening agents.

Non-aqueous suspensions can be formulated by suspending the active ingredient in a vegetable oil, for example, arachis oil, olive oil, sesame oil, or coconut oil, or in a mineral oil, for example liquid paraffin, and the suspension may contain a thickening agent, for example beeswax, hard paraffin or cetyl alcohol. These compositions can also contain a sweetening agent, flavoring agent and antioxidant.

The dosage of the compounds of formula I as antihypertensive agents will vary with the form of administration and the particular compound chosen. Furthermore, it will vary with the particular host as well as the age, weight and condition of the host under treatment as well as with the nature and extent of the symptoms. Generally, treatment is initiated with small dosages substantially less than the optimum dose of the compound. Thereafter, the dosage is increased by small increments until the optimum effect under circumstances is reached. In general, the compounds of this invention are most desirably administered at a concentration level that will generally afford effective results without causing any harmful or deleterious side effects. For example, the effective antihypertensive amount of the compounds for oral administration usually ranges from about 0.1 mg to about 250 mg per kilogram body weight per day in single or divided doses although as aforementioned variations will occur. However a dosage level that is in the range of from about 1.0 to about 100 mg per kilogram body weight per day in single or divided doses is employed most desirably for oral administration in order to achieve effective results.

The compound of formula I, or a therapeutically acceptable salt thereof, also can be used to produce beneficial effects in the treatment of hypertension, peripheral and cerebral vascular diseases and related disorders when combined with a therapeutically effective amount of a diuretic and/or antihypertensive agent commonly used in antihypertensive therapy. Such antihypertensive therapeutic agents include, for example, the thiazide diuretics for instance, chlorothiazide or hydrochlorothiazide; mineralocorticoid antagonizing diuretic agents, e.g., spironolactone; and other diuretics such as triameterene and furosemide. Examples of still other suitable antihypertensive agents are prazosin, hydralazine and centrally active antihypertensive agents such as methyldopa, clonidine, and reserpine; as well as the β-adrenergic blocking agents, for instance, propranolol. In this instance, the compound of formula I, or its therapeutically acceptable acid addition salt can be administered sequentially or simultaneously with the antihypertensive and/or diuretic agent. Preferred antihypertensive therapeutic agents are the antihypertensive agents such as the thiazides, mineralocorticoid antagonizing duiretic agents and the β-adrenergic blocking agents. A combination of the foregoing antihypertensive and/or diuretic agents, e.g. propranolol and hydrochlorothiazide, can be substituted for a single agent. Suitable methods of administration, compositions and dosages of the above described diuretic and/or antihypertensive agents are well known in the art; for instance, "Physician Desk Reference", 32 ed., Medical Economics Co., Oradell, N.J., U.S.A., 1978. For example, the agent propranolol is administered daily to humans in a range of 80 to 640 mg, usually in the form of unit doses of 10, 20, 40 or 80 mg. When used in combination, the compound of formula I, or its therapeutically acceptable salt is administered as described previously.

PROCESS

Reaction scheme 1 illustrates a preferred method for preparing the compounds of formula I in which $R^1$ is lower alkyl, lower alkenyl, lower alkylnyl, hydroxy(lower)alkyl, lower alkoxycarbonyl, formyl, phenyl(lower)alkyl, phenylcarbonyl, 2- or 3-furanylcarbonyl, phenyl, 2- or 3-pyridinyl, 1-oxo(lower)alkoxy(lower)alkyl, 2-imidazolinyl, α-halophenyl-α-phenylmethyl or phenyl substituted with one or two members selected from the group consisting of halo, lower alkyl, lower alkoxy or trifluoromethyl.

REACTION SCHEME 1

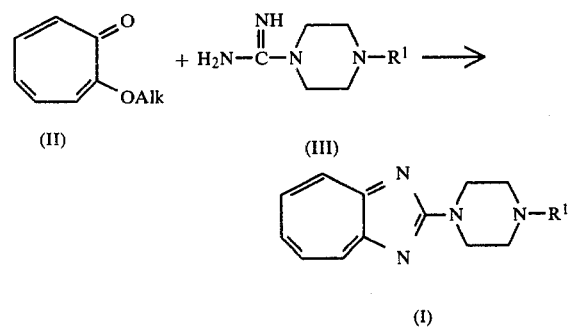

preparation and their interconversions by F. Pietra, Chem. Rev., 73, 293 (1973). Thus, the 2-alkoxy-tropones are either known or they can be prepared by conventional means.

A number of the starting materials of formula III are described in the chemical literature, for example, H. Kobayaski et al., 85, 160159 s (1976) for Japan Kokai, 76 39,680. Otherwise, the compounds of formula III are readily prepared from the appropriate piperazine derivative and this preparation is shown in reaction scheme 2.

REACTION SCHEME 2

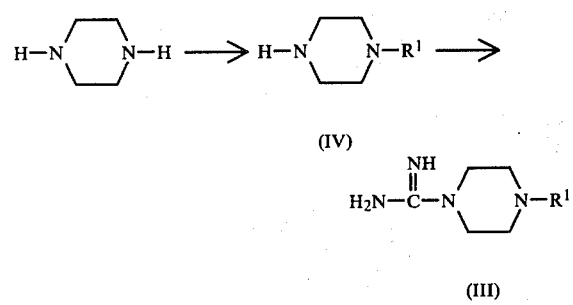

If required, piperazine is subjected to an alkylation or acylation type reaction according to conventional methods to obtain the corresponding piperazine derivative of formula IV in which $R^1$ is as defined immediately above. It should be noted that a rather large number of the piperazine derivatives of formula IV are either known or commercially available. Condensation of the compound of formula IV with 1.0 to 1.4 molar equivalents of a hydrobromide or hydroiodide salt of ethyl- or methyl-thiomethanimidamide in a solution of ethanol at 70° to 80° C. for two to ten hours gives the corresponding hydrobromide or hydroiodide salt of the compound of formula III.

Returning to reaction scheme 1, the 2-lower alkoxy-tropone derivative of formula II is condensed with about 1.0 to 1.3 molar equivalents of the hydrobromide or hydroiodide salt of the compound of formula III in which $R^1$ is as defined immediately above in the presence of 1.0 to 1.3 molar equivalents of a strong proton acceptor, preferably potassium or sodium lower alkoxide. The preferred lower alkoxide is selected from methoxide, ethoxide or propoxide. A suitable solvent for this condensation can be selected from a lower alkanol, preferably methanol, ethanol or propanol. The condensation reaction is maintained at 50° to 100° C. for 0.5 to 20 hours and the corresponding compound of formula I in which $R^1$ is as defined immediately above is isolated by conventional methods.

The above described compounds of formula I in which $R^1$ is lower alkoxycarbonyl can be converted to other compounds of formula I. In general, these conversions involve the alkaline hydrolysis of the lower alkoxycarbonyl group to obtain the corresponding secondary amine, i.e. $R^1 = H$. This secondary amine, then can be further subjected to various substitution reactions.

Treatment with alkali in the presence of water of the compound of formula I in which $R^1$ is lower alkoxycarbonyl, preferably with three to ten molar equivalents of sodium or potassium hydroxide in an inert solvent, preferably a mixture of water and a lower alkanol, at 50° to The 2-alkoxy-tropones of formula II suitable as starting materials are described in a number of reports; for example, see the review on tropone derivatives, their 100° C. for 10 to 30 hours gives the corresponding compound of formula I in which $R^1$ is hydrogen.

Reaction of the latter compound of formula I with 1.2 to 1.5 molar equivalents of the hydroiodide salt of methylthiomethanimidamide or 2-(methylthio)-imidazoline in a lower alkanol at 50° to 100° C. for two to ten hours affords the corresponding compound of formula I in which $R^1$ is aminoiminomethyl or 2-imidazolinyl.

If required, the lower alkoxycarbonyl can be easily introduced on the compound of formula I. This reaction involves the condensation of the compound of formula I in which $R^1$ is hydrogen with 1.0 to 1.5 molar equivalents of a lower alkyl ester of bromo- or chloroformic acid in the presence of 1.0 to 1.5 molar equivalents of an organic proton acceptor, preferably triethylamine, at 0° to 20° C. for one to ten hours to obtain the corresponding compound of formula I in which $R^1$ is lower alkoxycarbonyl. Any inert organic solvent can be used in this condensation, preferred solvents are selected from halogenated hydrocarbons, preferably methylene chloride or chloroform.

Another reaction of the compound of formula I in which $R^1$ is hydrogen makes use of an alkylation type reaction. Reaction of the latter compound of formula I with 1.0 to 1.3 molar equivalents of a lower alkyl, lower alkenyl or lower alkynyl bromide or iodide in the presence of 1.0 to 1.3 basic equivalents of a proton acceptor, preferably 0.5 to 0.65 molar equivalents of potassium carbonate, in an inert solvent, preferably dimethylsulfoxide, at 5° to 40° C. for one to ten hours gives the corresponding compound of formula I in which $R^1$ is lower alkyl, lower alkenyl or lower alkynyl.

The compound of formula I in which $R^1$ is sodium thiothioxomethyl is obtained by reacting the corresponding compound of formula I in which $R^1$ is hydrogen with 1.0 to 1.3 molar equivalents of each of carbon disulfide and sodium or potassium hydroxide in an inert solvent, preferably a mixture of water and a lower alkanol, at 0° to 10° C. for 0.5 to 5 hours.

Reaction of the compound of formula I in which $R^1$ is sodium thiothioxomethyl with 1.5 to 10 molar equivalents of a lower alkyl bromide or iodide in an inert organic solvent, preferably a lower alkanol, at 0° to 30° C. for one to ten hours gives the corresponding compound of formula I in which $R^1$ is (lower alkylthio)thioxomethyl.

Hydrazinolysis of the latter compound of formula I, preferably when $R^1$ is (methylthio)thioxomethyl, with 10 to 30 molar equivalents of hydrazine hydrate in an inert solvent, preferably a lower alkanol or dimethylformamide, at 50° to 100° C. for 5 to 15 hours provides the corresponding compound of formula I in which $R^1$ is hydrazinothioxomethyl.

Reaction of the compound of formula I in which $R^1$ is hydrogen with 1.0 to 1.3 molar equivalents of phenyl or lower alkyl isothiocyanate in an inert organic solvent, preferably benzene or toluene, at 0° to 30° C. for 5 to 60 minutes gives the corresponding compound of formula I in which $R^1$ is (phenylamino)thioxomethyl or (lower alkylamino)thioxomethyl.

Similarly, reaction of the compound of formula I in which $R^1$ is hydrogen with 1.0 to 1.3 molar equivalents of benzoyl isothiocyanate in an inert organic solvent, preferably benzene or toluene, at 0° to 30° C. for 5 to 60 minutes gives the corresponding intermediate having the (benzoylamino)thioxomethyl group on the nitrogen. Hydrolysis of this intermediate with an aqueous solution of four to ten molar equivalents of potassium or sodium hydroxide at 80° to 120° C. for 10 to 30 hours affords the corresponding compound of formula I in which $R^1$ is aminothioxomethyl.

The above described compounds of formula I in which $R^1$ is hydroxy(lower)-alkyl can also be converted to other compounds of formula I. In this conversion, the compound of formula I in which $R^1$ is hydroxy(lower-)alkyl is reacted with 1.0 to 1.3 molar equivalents of a lower alkanoyl bromide or chlorine in the presence of 1.0 to 1.3 molar equivalents of an organic proton acceptor, preferably triethylamine, in an inert organic solvent, preferably methylene chloride or chloroform, at 10° to 30° C. for 10 to 30 hours to obtain the corresponding compound of formula I in which $R^1$ is 1-oxo(-lower)alkoxy(lower)alkyl.

The following Examples illustrate further this invention.

EXAMPLE 1

4-(2-CYCLOHEPTIMIDAZOLYL)-PIPERAZINE-1-CARBOXYLIC ACID ETHYL ESTER (I: $R^1$ is ethoxycabonyl)

A mixture of 1-(aminoiminomethyl)-piperazine-4-carboxylic acid ethyl ester hydroiodide (3.6 g) and sodium (0.275 g) in ethanol (15 ml) was stirred at room temperature for 15 min. A solution of 2-methoxy-2,4,6-cycloheptatrien-1-one (1.36 g) in ethanol (3 ml) was added dropwise. The mixture was refluxed for 1.25 hr, cooled and evaporated. The residue was dissolved in a mixture of water and ethyl acetate. The organic phase was separated, dried and evaporated. The residue was chromatographed through silica gel using ethyl acetate-benzene (7:3) and the eluates were evaporated. The residue (1.1 g) was crystallized from chloroformhexane to obtain the title compound: mp 136°–138° C.; nmr(CDCl$_3$) δ1.3(3H,t), 3.35-(4H,m), 3.67(4H,m), 4.2(2H,q) and 6.9(5H,m); ir (CHCl$_3$) 1690 and 1570 cm$^{-1}$; uv max (MeOH) 350(ε9,679), 254(ε13,089) and 225 nm (ε12,171) and Anal. Calcd for $C_{15}H_{18}N_4O_2$: C, 62.91% H, 6.33% N, 19.57% and Found: C, 62.55% H, 6.26% N, 19.55%.

A saturated solution (6 ml) of hydrogen chloride in diethyl ether was mixed with a suspension of the title compound (1.4 g) in methanol (3 ml) and diethyl ether (4 ml). The mixture was stirred for 10 min and filtered. The precipitate was crystallized from methanol-diethyl ether to obtain the hydrochloride salt (1.36 g) of the title compound: mp 218°–200° C.; ir (nujol) 2300, 1703 and 1645 cm$^{-1}$; uv max (MeOH) 254 (ε22,885) and 231 nm(ε25,855) and nmr(DMSO-d$_6$)δ 1.22(3H,t), 3.6(4H,m), 4.0(6H, m), 8.3(5H,m) and 11.5(2H,s).

In the same manner but replacing 1-(aminoiminomethyl)-piperazine-4-carboxylic acid ethyl ester with an equivalent amount of 1-(aminoiminomethyl)-3-ethylpiperazine-4-carboxylic acid methyl ester, 1-(aminoiminomethyl)-piperazine-4-carboxylic acid 2-methylpropyl ester or 1-(aminoiminomethyl)-3-methylpiperazine-4-carboxylic acid propyl ester, the following compounds of formula I are obtained, respectively: 4-(2-cycloheptimidazolyl)-3-ethylpiperazine-1-carboxylic acid methyl ester, 4-(2-cycloheptimidazolyl)-piperazine-1-carboxylic acid 2-methylpropyl ester and 4-(2-cycloheptimidazolyl)-3-methylpiperazine-1-carboxylic acid propyl ester.

Similarly by replacing 2-methoxy-2,4,6-cycloheptatriene-1-one with an equivalent amount of 5-bromo-2-methoxy-2,4,6-cycloheptatriene-1-one, 2-methoxy-5- propyl-2,4,6-cycloheptatriene-1-one, 5-ethoxy-2-methoxy-2,4,6-cycloheptatriene-1-one or 2-methoxy-5-trifluoromethyl-2,4,6-cycloheptatriene-1-one, the following compounds of formula I are obtained, respectively; 4-(6-bromo-cycloheptimidazole-2-yl)-piperazine-1-carboxylic acid ethyl ester, 4-(6-propyl-cycloheptimidazol-2-yl)-piperazine-1-carboxylic acid ethyl ester, 4-(6-ethoxy-cycloheptimidazol-2-yl)-piperazine-1-carboxylic acid ethyl ester and 4-(6-trifluoromethyl-cycloheptimidazol-2-yl)-piperazine-1-carboxylic acid ethyl ester.

EXAMPLE 2

2-(1-PIPERAZINYL)CYCLOHEPTIMIDAZOLE
(I: $R^1$ is hydrogen)

A mixture of 4-(2-cycloheptimidazolyl)-piperazine-1-carboxylic acid ethyl ester (2.86 g, described in Example 1) and potassium hydroxide in ethanol (20 ml) and water (1.5 ml) was refluxed for 20 hr. Water was added and the ethanol was evaporated. Additional water was added and the solution was extracted with chloroform. The organic extract was dried and evaporated to give the title compound (2.7 g). To a solution of the title compound in chloroform and diethyl ether, a solution of hydrogen chloride in diethyl ether was added. The precipitate was collected and crystallized from methanol-diethyl ether to obtain the hydrochloride salt of the title compound (2.4 g): mp>280° C.; ir(nujol) 2600, 1630 and 1584 cm$^{-1}$; uv max (MeOH) 285($\epsilon$7540), 261($\epsilon$26,930) and 236 nm($\epsilon$18,310) and nmr(DMSO-d$_6$)$\delta$ 3.37(4H,t), 4.3(4H,t), 8.4(5H,m) and 10.0(2H,s).

In the same manner but replacing 4-(2-cycloheptimidazolyl)-piperazine-1-carboxylic acid ethyl ester with an equivalent amount of another compound of formula I described in Example 1, the following different compounds of formula I are obtained, respectively; 2-(3-ethyl-1-piperazinyl)cycloheptimidazole, 2-(3-methyl-1-piperazinyl)cycloheptimidazole, 6-bromo-2-(1-piperazinyl)cycloheptimidazole, 6-propyl-2-(1-piperazinyl)cycloheptimidazole, 6-ethoxy-2-(1-piperazinyl)cycloheptimidazole, and 6-trifluoromethyl-2-(1-piperazinyl)cycloheptimidazole.

EXAMPLE 3

4-(2-CYCLOHEPTIMIDAZOLYL)-1-PIPERAZINECARBOXIMIDAMIDE (I: $R^1$ is aminoiminomethyl)

A mixture of 2-(1-piperazinyl)cycloheptimidazole (3.5 g, described in Example 2) and methylthiocarboximidamide hydroiodide (3.9 g) was refluxed for 4hr and evaporated. The residue was dissolved in water (40 ml) and the solution was cooled. The precipitate was collected and crystallized from methanol to obtain the hydroiodide trihydrate salt (3.6 g) of the title compound. mp>280° C.; ir (nujol) 3330, 3160, 1665, 1625 and 1600 cm$^{-1}$; uv max (MeOH) 263 nm($\epsilon$26,590); nmr(DMSO-d$_6$)$\delta$3.6(4H), 3.97(4H), 7.4(4H) and 7.85(5H) and Anal. Calcd for C$_{13}$H$_{16}$N$_6$.HI.3H$_2$O: C, 35.59% H, 5.24% N, 19.17% and Found: C, 35.73% H, 4.95% N, 18.62%.

In the same manner but replacing methylthiocarboximidamide wth an equivalent amount of 2-(methylthio)imidazoline, the hydroiodide salt of 2-[4-(2-imidazolinyl)-1-piperazinyl]-cycloheptimidazole (I: $R^1$ is 2-imidazolinyl) was obtained: mp>280° C. (crystallized from methanol): ir (nujol) 3420, 3200, 1650, 1600 and 1526 cm$^{-1}$; uv max (H$_2$O) 263 ($\epsilon$29,565) and 233 nm ($\epsilon$29,040); nmr (DMSO-d$_6$) $\delta$3.70 (4H,m), 3.75(4H,s), 4.05(4H,m), 7.9(5H,m) and 8.45(2H,m) and Anal. Calcd for C$_{15}$H$_{18}$N$_6$ HI: C, 43.95% H, 4.68% N, 20.48% and Found: C, 43.87% H, 4.68% N, 19.82%.

In the same manner but replacing 2-(1-piperazinyl)cycloheptimidazole with an equivalent amount of another compound of formula I described in Example 2, the following compounds of formula I are obtained, respectively: 4-(2-cycloheptimidazolyl)-3-ethyl-1-piperazinecarboximidamide, 4-(2-cycloheptimidazolyl)-3-methyl-1-piperazinecarboximidamide, 4-(6-bromo-2-cycloheptimidazolyl)-1-piperazinecarboximidamide, 4-(6-propyl-2-cycloheptimidazolyl)-1-piperazinecarboximidamide, 4-(6-ethoxy-2-cycloheptimidazolyl)-1-piperazinecarboximidamide, and 4-(6-trifluoromethyl-2-cycloheptimidazolyl)-1-piperazinecarboximidamide.

EXAMPLE 4

4-(2-CYCLOHEPTIMIDAZOLYL)-PIPERAZINE-1-CARBOXYLIC ACID 2-METHYLPROPYL ESTER (I: $R^1$ is 2-methylpropoxycarbonyl)

A solution of 2-methylpropyl chlorofromate (1.65 g) in methylene chloride (2 ml) was added dropwise to a solution at 0° to 5° C. of 2-(1-piperazinyl)cycloheptimidazole (2.14 g, described in Example 2) and triethylamine (1.1 g) in methylene chloride (4 ml). The mixture was stirred at room temperature for 2 hr. Water was added and the mixture was extracted with methylene chloride. The organic extract was dried and evaporated. The residue was filtered with diethyl ether to obtain a precipitate (2.97 g) which was crystallized from chloroform-hexane to obtain the title compound: mp 130°-133° C.; ir (CHCl$_3$) 1685, 1600, 1565 and 1525 cm$^{-1}$; uv max (MeOH) 239($\epsilon$25,630), 263 ($\epsilon$26,445) and 242 nm ($\epsilon$7,290) and nmr-(CDCl$_3$) $\delta$ 3.55(4H,m), 3.9(6H,m) and 7.65(5H,m).

EXAMPLE 5

2-[4-(2-PROPENYL)-1-PIPERAZINYL]-CYCLOHEPTIMIDAZOLE (I: $R^1$ is 2-propenyl)

A mixture of 2-(1-piperazinyl)cycloheptimidazole (3.15 g, described in Example 2) and potassium carbonate (1.14 g) in dimethyl sulfoxide (10 ml) was stirred for 15 min and a solution of 2-propenyl bromide (1.18 g) in dimethyl sulfoxide was added. The reaction mixture was stirred for 2.5 hr and diluted with brine. The solution was extracted with ethyl acetate and the organic extract was dried and evaporated to give the title compound (1.8 g): mp 108°-111° C.; ir(CHCl$_3$) 1600, 1565 and 1520 cm$^{-1}$; uv max (MeOH) 263($\epsilon$29,965), 237($\epsilon$25,490) and 362 nm ($\epsilon$21,620) and nmr(CDCl$_3$)$\delta$ 2.6(4H,s), 3.0(2H,d), 4.05(4H,t), 5.15(2H,m), 5.75(1H,m) and 7.65(5H,m).

In the same manner but replacing 2-propenyl bromide with an equivalent amount of 2-propynyl bromide, 2-[4-(2-propynyl)-1-piperazinyl]-cycloheptimidazole (I: $R^1$ is 2-propynyl) was obtained: mp 88°-89° C. (crystallized from methanol); ir-(CHCl$_3$) 3300, 1630, 1565 and 1520 cm$^{-1}$; uv max (MeOH) 237 ($\epsilon$25.810), 263 ($\epsilon$29,625) and 292 nm ($\epsilon$7,310); nmr (CDCl$_3$) $\delta$2.27(1H,t), 2.75(4H,t), 3.4(2H,d), 4.1(4H,t) and 7.7(5H,m) and Anal. Calcd for C$_{15}$H$_{16}$H$_4$: C, 71.40% H, 6.39% N, 22.21% and Found: C, 71.31% H, 6.39% N, 22.36%.

Similarily, by replacing 2-(1-piperazinyl)cycloheptimidazole with an equivalent amount of another compound of formula I described in Example 2, the following compounds of formula I are obtained, respectively:

2-[3-ethyl-4-(2-propenyl)-1-piperazinyl]-cycloheptimidazole, 2-[3-methyl-4-(2-propenyl)-1-piperazinyl]-cycloheptimidazole, 6-bromo-2-[4-(2-propenyl)-1-piperazinyl]-cycloheptimidazole, 6-propyl-2-[4-(2-propenyl)-1-piperazinyl]-cycloheptimidazole, 6-ethoxy-2-[4-(2-propenyl)-1-piperazinyl]-cycloheptimidazole and 6-trifluoromethyl-2-[4-(2-propenyl)-1-piperazinyl]-cycloheptimidazole.

EXAMPLE 6

4-(2-CYCLOHEPTIMIDAZOLYL)-PIPERAZINE-1-CARBOTHIOIC ACID, SODIUM SALT (I: $R^1$ is sodium thiothioxomethyl)

A solution of carbon disulfide (0.76 g) in ethanol (2.5 ml) was added to a solution at 5° C. of 2-(1-piperazinyl)-cycloheptimidazole (2.14 g, described in Example 2) and sodium hydroxide (0.392 g) in water (1 ml) and ethanol (6 ml). The resulting mixture was stirred at 5° C. for 1.5 hr and filtered. The precipitate was washed with ethanol-diethyl ether to give a crude product (2.67 g) which was crystallized from methanol-diethyl ether to give the title compound: ir (nujol) 3340, 3260, 1570, 1600 and 1527 cm$^{-1}$; uv max (MeOH) 291 ($\epsilon$16,690), 263($\epsilon$33,165) and 239 nm ($\epsilon$25,830) and nmr (MeOH-d$_4$) $\delta$3.95(4H,m), 4.65(4H,m) and 7.85(5H,m).

In the same manner but replacing 2-(1-piperazinyl)cycloheptimidazole with an equivalent amount of another compound of formula I described in Example 2, the following compounds of formula I are obtained, respectively: 3-ethyl-4-(2-cycloheptimidazolyl)-piperazine-1-carbothioic acid, sodium salt; 3-methyl-4-(2-cycloheptimidazolyl)-piperazine-1-carbothioic acid, sodium salt; 4-(6-bromo-(2-cycloheptimidazolyl)-piperazine-1-carbothioic acid, sodium salt; 4-(6-propyl-(2-cycloheptimidazolyl)-piperazine-1-carbothioic acid, sodium salt; 4-(6-ethoxy-(2-cycloheptimidazolyl)-piperazine-1-carbothioic acid, sodium salt and 4-(6-trifluoromethyl-(2-cycloheptimidazolyl)-piperazine-1-carbothioic acid, sodium salt.

EXAMPLE 7

4-(2-CYCLOHEPTIMIDAZOLYL)-PIPERIZINE-1-CARBODITHOIC ACID, S-METHYL ESTER (I: $R^1$ is (methylthio)thioxomethyl)

To a suspension of 4-(2-cycloheptimidazolyl)-piperazine-1-carbothioic acid, sodium salt (5 g, described in Example 6) in ethanol at 0° C. (20 ml) was added a solution of methyl iodide (22.8 g) in ethanol (40 ml) over a period of 45 min. The mixture was further stirred for 1 hr at 0° C. The reaction mixture was filtered to yield a crude residue (3.4 g). The residue was crystallized from chloroform-diethyl ether to give the title compound (1.7 g): mp 270°-272° C.; ir (nujol) 1607, 1577 and 1533 cm$^{-1}$; uv max (MeOH) 263 ($\epsilon$36,225) and 240 nm($\epsilon$25,050); nmr(CDCl$_3$) $\delta$2.72-(3H,s), 4.2(8H,m) and 7.8(5H,m) and Anal. Calcd for $C_{14}H_{16}N_4S_2$: C, 55.26% H, 5.48% H, 19.18% and Found: C, 55.51% H, 5.24% N, 19.17%.

In the same manner but replacing 4-(2-cycloheptimidazolyl)-piperazine-1-carbothioic acid, sodium salt with an equivalent amount of another compound of formula I described in Example 6, the following compounds of formula I are obtained, respectively: 3-ethyl-4-(2-cycloheptimidazolyl)-piperazine-1-carbothioic acid S-methyl ester, 3-methyl-4-(2-cycloheptimidazolyl)-piperazine-1-carbothioic acid S-methyl ester, 4-(6-bromo-2-cycloheptimidazolyl)-piperazine-1-carbothioic acid S-methyl ester, 4-(6-propyl-2-cycloheptimidazolyl)-piperazine-1-carbothioic acid S-methyl ester, 4-(6-ethoxy-2-cycloheptimidazolyl)-piperazine-1-carbothioic acid S-methyl ester and 4-(6-trifluoromethyl-2-cycloheptimidazolyl)-piperazine-1-carbothioic acid S-methyl ester.

EXAMPLE 8

4-(2-CYCLOHEPTIMIDAZOLYL)-PIPERAZINE-1-CARBOTHIOIC ACID HYDRAZIDE (I: $R^1$ is hydrazinothioxomethyl)

To a suspension of 4-(2-cycloheptimidazolyl)-piperazine-1-carbothioic acid S-methyl ester (0.8 g, described in Example 7) in methanol (5 ml) was added hydrazine hydrate (2.63 g). The reaction mixture was heated to 70° C. for 6 hrs and evaporated. The residue was suspended in diethyl ether and filtered to give a solid (0.61 g). The solid was crystallized from dimethylformamide to give the title compound (0.4 g): mp 224°-228° C.; ir (nujol) 3200 and 3120 cm$^{-1}$; uv max (MeOH) 257($\epsilon$34,810) and 242 nm($\epsilon$32,840) and nmr(DMSO-d$_6$)$\delta$ 3.9(8H,s) and 7.8(5H,m).

In the same manner but replacing 4-(2-cycloheptimidazolyl)-piperazine-1-carbothioic acid, sodium salt with an equivalent amount of another compound of formula I described in Example 7, the following compounds of formula I are obtained, respectively: 3-ethyl-4-(2-cycloheptimidazolyl)-piperazine-1-carbothioic acid hydrazide, 3-methyl-4-(2-cycloheptimidazolyl)-piperazine-1-carbothioic acid hydrazide, 4-(6-bromo-2-cycloheptimidazolyl)-piperazine-1-carbothioic acid hydrazide, 4-(6-propyl-2-cycloheptimidazolyl)-piperazine-1-carbothioic acid hydrazide, 4-(6-ethoxy-2-cycloheptimidazolyl)-piperazine-1-carbothioic acid hydrazide, 4-(6-trifluoromethyl-2-cycloheptimidazolyl)-piperazine-1-carbothioic acid hydrazide.

EXAMPLE 9

4-(2-CYCLOHEPTIMIDAZOLYL)-PIPERAZINE-1-CARBOTHIOAMIDE (I: $R^1$ is aminothioxomethyl)

To a solution of 2-(1-piperazinyl)cycloheptimidazole(1.5 g, described in Example 2) in dry benzene (3 ml), was added a solution of benzoyl isocyanate (1.25 g) in benzene (3 ml) at room temperature. The reaction mixture was diluted with diethyl ether-hexane and the precipitate was filtered and dried to yield N-benzoyl-4-(2-cycloheptimidazolyl)-piperazine-1-carbothioamide (2.54 g); mp 182°-185° C. and nmr(DMSO-d$_6$) $\delta$4.0(8H,s) and 7.6(10H,m). A mixture of the latter compound (2.1 g) and sodium hydroxide (1.4 g) in water (11 ml) was heated at 110° C. for 20 hr, cooled and filtered. The precipitate was dried to give the title compound (0.97 g): mp 245°-247° C.; ir (nujol) 3390, 3290, 1620, 1603 and 1570 cm$^{-1}$; uv max (MeOH) 256 nm ($\epsilon$38,270); nmr(DMSO-d$_6$) $\delta$3.95(8H,s) and 7.8(5H,m) and Anal. Calcd for $C_{13}H_{15}H_5S$: C, 57.12% H, 5.53% N, 25.62% and Found: C, 57.52% H, 5.64% N, 25.59%.

EXAMPLE 10

4-(2-CYCLOHEPTIMIDAZOLYL)-N-PHENYL-PIPERAZINE-1-CARBOTHIOAMIDE (I: $R^1$ is (phenylamino)thioxomethyl)

To a solution of 2-(1-piperazinyl)cycloheptimidazole(1.5 g, described in Example 2) in benzene (3 ml) was added a solution of phenyl isocyanate (1.04 g) in benzene (3 ml). The yellow precipitate thus formed was filtered with diethyl ether and dried to yield crude product (2.3 g). Crystallization from dimethylformamide-water gave the title compound (2.0 g): mp 267°–269° C.; ir(nujol) 3310 and 1460 cm$^{-1}$; uv max (MeOH) 262 ($\epsilon$44,430) and 241 nm ($\epsilon$33,190) and nmr (DMSO-d$_6$) δ4.05(8H,m), 7.6(10H,m) and 9.4(1H,s) and Anal. Calcd for C$_{19}$H$_{19}$N$_5$S: C, 65.30% H, 3.48% N, 20.04% and Found: C, 65.17% H, 5.46% N, 19.79%.

In the same manner but replacing phenyl isocyanate with an equivalent amount of methyl isothiocyanate, 4-(2-cycloheptimidazolyl)-N-methyl-piperazine-1-carbothioamide (I: R$^1$ is (methylamino)thioxomethyl) was obtained: mp 267°–269° C.; ir(nujol) 3320 and 1460 cm$^{-1}$; uv max (MeOH) 291($\epsilon$7,980) and 252 nm ($\epsilon$37,910); nmr-(DMSO-d$_6$) δ2.95(3H,d), 3.95(8H,s) and 7.85 (5H,m) and Anal. Calcd for C$_{14}$H$_{17}$H$_5$S: C, 58.51% H, 5.91% N, 24.37% and Found: C, 58.44% H, 5.91% N, 24.12%.

EXAMPLE 11

1-(2-FURANYLCARBONYL)PIPERAZINE (V: R$^1$=2-furanylcarbonyl)

Piperazine (8.6 g) was dissolved in water (200 ml) then 2 N hydrochloric acid (120 ml) and acetone (200 ml) was added. The pH was adjusted to pH 3 with a pH meter (using a 40 g sodium acetate in 100 ml water solution) monitoring the reaction constantly. The reaction mixture was heated to 80° C. and 2-furoyl chloride (13.04 g) was added dropwise and when the pH decreased to below 3.0 a drop of sodium acetate solution was added to bring it back to 3.0±0.2. When all the 2-furoyl was added while keeping the pH at 3.0±0.2 the reaction mixture was stirred for one hour at 80° C. The solvent was evaporated and the residue was extracted with boiling anhydrous ethanol. The ethanol extract was filtered and allowed to stand at room temperature to crystallized out 10.26 g of 1-(2-furanylcarbonyl)-piperazine hydrochloride, mp 206°–208° C. The latter salt (13.9 g) was combined with N sodium hydroxide and the mixture was extracted with chloroform. The organic extract was dried over sodium sulfate and evaporated to give a residue (9.5 g) of the title compound.

In the same manner but replacing a 2-furoyl chloride with an equivalent amount of benzoyl chloride; 1-benzoylpiperazine hydrochloride, mp 278° C., and 1-benzoylpiperazine were obtained.

Similarily, by replacing 1-(2-furanylcarbonyl)piperazine hydrochloride with an equivalent amount of 1-(3-chlorophenyl)piperazine hydrochloride, 1-(3-chlorophenyl)piperazine is obtained.

EXAMPLE 12

4-(2-FURANYLCARBONYL)-1-PIPERAZINECARBOXIMIDAMIDE (III: R$^1$=2-furanylcarbonyl)

A mixture of 4-(2-furanylcarbonyl)piperazine (1.8 g, described in Example 11) and methylthiocarboximidamide hydroiodide (2.62 g) in ethanol (6 ml) was refluxed for 3 hr. The mixture was diluted with 10 ml of ethanol and 20 ml of diethyl ether to obtain the hydroiodide salt of the title compound (1.8 g), mp 192°–194° C.

In the same manner but replacing 4-(2-furanylcarbonyl)piperazine with an equivalent amount of 4-benzoylpiperazine (described in Example 11), 4-(phenylmethyl)piperazine, 4-phenylpiperazine or 4-formylpiperazine and using the hydrobromide salt of methylthiocarboximidamide, the following compounds of formula III were obtained, respectively: 4-benzoyl-1-piperazinecarboximidamide hydrobromide, 4-(phenylmethyl)-1-piperazinecarboximidamide hydrobromide, mp 199°–201° C., 4-phenyl-1-piperazinecarboxidamide hydrobromide, mp 150°–152° C., and 4-formyl-1-piperazinecarboximidamide hydrobromide, mp 212°–213° C.

EXAMPLE 13

2-(4-METHYL-1-PIPERAZINYL)CYCLOHEPTIMIDAZOLE (I: R$^1$ is methyl)

4-Methyl-1-piperazinecarboximidamide hydroiodide (17.8 g) was suspended in ethanol (15 ml). Sodium (1.5 g) in ethanol (47.8 ml) was added to it. The mixture was stirred at room temperature for 30 min. A solution of 2-methoxy-2,4,6-cycloheptatrien-1-one in ethanol (12 ml) was added dropwise. The mixture was refluxed for 3 hr and evaporated. The residue was taken in water and extracted with ethyl acetate in a continuous extractor. The organic layer was dried and evaporated. The residue was chromatographed through a column of silica gel using 5% methanol in chloroform and the eluates were evaporated. The residue was taken up in diethyl ether and filtered. The precipitate was crystallized from diethyl ether-hexane to obtain the title compound (3.4 g): mp 93°–95° C.; ir (CHCl$_3$) 1600, 1565 and 1523 cm$^{-1}$; uv max (MeOH) 291 ($\epsilon$7,280), 262($\epsilon$28,445) and 238 nm($\epsilon$23,970); nmr-(CDCl$_3$) δ 2.3(3H,s), 2.5(4H,t), 4.0(4H,t) and 7.2–8.0(5H,m) and Anal. Calcd for C$_{13}$H$_{16}$N$_4$: C, 68.39% H, 7.06% N, 24.54% N, 24.54% and Found: C, 68.45% H, 6.99% N, 24.27%.

A saturated solution of hydrogen chloride in diethyl ether (6 ml) was added to a solution of the title compound (1.5 g) in diethyl ether-chloroform (10:1, 55 ml). The mixture was stirred for 10 min and filtered. The precipitate was washed with diethyl ether, dried and crystallized from methanol-diethyl ether to obtain the hydrochloride salt of the title compound (1.82 g): mp 263°–265° C.; ir(nujol) 3400, 2430, 1633, 1620 and 1584 cm$^{-1}$; uv max (MeOH) 356($\epsilon$16,600), 289 ($\epsilon$7,350), 261($\epsilon$26,750) and 235 nm($\epsilon$17,400) and nmr(DMSO-d$_6$)δ 2.8(3H,s), 3.5(8H,m) and 8.3(5H,m).

In the same manner but replacing 2-methoxy-2,4,6-cycloheptatrien-1-one with an equivalent amount of 5-iodo-2-methoxy-2,4,6-cycloheptatrien-1-one, 5-propyl-2-methoxy-2,4,6-cycloheptatrien-1-one or 5-butoxy-2-methoxy-2,4,6-cycloheptatrien-1-one, the following compounds of formula I are obtained, respectively: 6-iodo-(4-methyl-1-piperazinyl)cycloheptimidazole, 5-propyl-2-(4-methyl-1-piperazinyl)cycloheptimidazole and 5-butoxy-2-(4-methyl-1-piperazinyl)cycloheptimidazole.

Similarly by replacing 4-methyl-1-piperazinecarboximidamide with an equivalent amount of 3-ethyl-4-propyl-1-piperazinecarboximidamide, 3-pentyl-4-ethyl-1-piperazinecarboximidamide or 3-methyl-4-(2-methylbutyl)-1-piperazinecarboximidamide, the following compounds of formula I are obtained, respectively; 2-(3-ethyl-4-propyl-1-piperazinyl)cycloheptimidazole, 2-(3-pentyl-4-ethyl-1-piperazinyl)cycloheptimidazole and 2-[3-methyl-4-(2-methylbutyl)-1-piperazinyl]cycloheptimidazole.

EXAMPLE 14

2-[4-[2-FURANYLCARBONYL)-1-PIPERAZINYL]CYCLOHEPTIMIDAZOLE (I: $R^1$ is 2-furanylcarbonyl)

A solution of 4-(2-furanylcarbonyl)-1-piperazinecarboximidamide (0.35 g, described in Example 12) in ethanol (5 ml) was treated with 1N ethanolic sodium ethoxide (1 ml) and 2-methoxy-2,4,6-cycloheptatrien-1-one (0.136 g) was added. The reaction mixture was refluxed for 4 hr and evaporated. The residue was taken up in water and extracted with ethyl acetate. After drying, the ethyl acetate extract was evaporated to yield 250 mg of residue. It was chromatographed through a column of silica gel with ethyl acetate and the residue of the pure fractions was crystallized from ethyl acetate to obtain the title compound (0.12 g): mp 172°–173° C.; ir (mull) 3102, 3095, 1623, 1601, 1571, 1525 and 1475 cm$^{-1}$; uv max(MeOH) 264($\epsilon$39,460), and 240 nm($\epsilon$33,420); nmr(CDCl$_3$) $\delta$ 4.0(8H,m) and 6.4–8.1(8H,m) and Anal. Calcd for $C_{17}H_{16}N_4O_2$: C, 66.21% H, 5.23% N, 18.17% and Found: C, 66.68% H, 5.14% N, 18.17%.

In the same manner but replacing 4-(2-furanylcarbonyl)-1-piperazinecarboximidamide hydroiodide with an equivalent amount of another compound of formula III, described in Example 12, the following compounds of formula I were obtained, respectively: 2-(4-benzoyl-1-piperazinyl)cycloheptimidazole: (I: $R^1$ is benzoyl) mp 148°–149° C.(ethyl acetate); ir(mull)1623 cm$^{-1}$ and uv max(MeOH) 289($\epsilon$30,340), 263($\epsilon$29,700) and 239 nm($\epsilon$7,950); 2-[4-(phenylmethyl)-1-piperazinyl]cycloheptimidazole: (I: $R^1$ is phenylmethyl) mp 97°–99° C.(ethyl acetate); ir(CHCl$_3$) 3660, 3330, 1600, 1565, 1525, 1495 and 697 cm$^{-1}$; uv max (MeOH) 295 ($\epsilon$6,750), 251($\epsilon$26,440) and 238 nm($\epsilon$25,860); nmr (CDCl$_3$)$\delta$2.6(4H,t), 3.57(2H,s), 4.05(4H,t) and 7.35–8.15(10H,m) and Anal. Calcd for $C_{19}H_{20}N_4$: C, 74.90% H, 6.65% N, 18.45% and Found: C, 74.63% H, 6.60% N, 77.65%; 2-(4-phenyl-1-piperazinyl)cycloheptimidazole: (I: $R^1$ is phenyl) mp 210°–212° C. (ethyl acetate); ir(mull) 1595, 1570, 1530 and 1503 cm$^{-1}$; uv max (MeOH) 288($\delta$7,960), 260($\epsilon$34,040) and 241 nm($\epsilon$29,530); nmr(CDCl$_3$)$\delta$3.35(4H,t), 4.23(4h,t) and 7.5(10H,m) and Anal. Calcd. for $C_{18}H_{18}N_4O$: C, 74.46% H, 6.25%, N, 19.29% and Found C, 74.12% H, 6.07% N, 19.16%; and 2-(4-formyl-1-piperazinyl)cycloheptimidazole: (I: $R^1$ is formyl) mp 165°–167° C. (ethyl acetate); ir(mull) 1670 cm$^{-1}$; nmr(CDCl$_3$)$\delta$ 3.9(8H,m) and 7.9(6H,m) and Anal. Calcd for $C_{13}H_{14}N_4O$: C, 64.43% H, 5.82% N, 23.12% and Found: C, 64.44% H, 5.80% N, 22.66%.

EXAMPLE 15

2-[4-(3-CHLOROPHENYL)-1-PIPERAZINYL]CYCLOHEPTIMIDAZOLE (I: $R^1$ is 3-chlorophenyl)

A mixture of 1-(3-chlorophenyl)piperazine (13 g, described in Example 11) and methylthiomethanimidamide hydrobromide (12.2 g) in ethanol (50 ml) was refluxed for 14 hr and evaporated. To the residue, 1N sodium ethoxide in ethanol (66 ml) and 2-methoxy-2,4,6-cycloheptatrien-1-one(9 g) were added. The mixture was refluxed for 2 hr and evaporated. The residue was chromatographed through a column of silica gel using ethyl acetate and the eluates were evaporated. The residue was crystallized from ethyl acetate to obtain the title compound (5.9 g): mp 217°–219° C; ir(mull)1615, 1590, 1575 and 1530 cm$^{-1}$; uv max (MeOH) 289($\epsilon$9.870), 261($\epsilon$43,230) and 240 nm($\epsilon$29,040); nmr(CDCl$_3$) $\delta$ 3.33(4H,t), 4.18(4H,t) and 7.5(9H,m) and Anal. Calcd for $C_{18}H_{17}N_4Cl$: C, 66.56% H, 5.27% N, ;b 17.25% and Found: C, 66.11% H, 5.10% N, 16.99%.

In the same manner but replacing 1-(3-chlorophenyl)piperazine with an equivalent amount of 1-piperazineethanol, 1-(4-chlorophenyl)piperazine, 1-(2-pyridinyl)piperazine, 1-(2-methylphenyl)piperazine, 1-(4-methoxyphenyl)piperazine, 1-(4-fluorophenyl)piperazine, 1-(3-trifluoromethylphenyl)piperazine, 1-(2-methoxyphenyl)-piperazine, 1-[$\alpha$,$\alpha$-(4'-chloro)diphenylmethyl]piperazine or 1-[4-(1-piperazinyl)-phenyl]-1-ethanone, the following compounds of formula I were obtained, respectively: 4-(2-cycloheptimidazolyl)-1-piperazineethanol: (I: $R^1$ is 2-hydroxyethyl) mp 136°–137° C. (crystallized from ethyl acetate); ir(mull) 3400, 1600, 1570 and 1526 cm$^{-1}$; uv max (MeOH) 293($\epsilon$7,490), 262($\epsilon$28,410) and 239 nm($\epsilon$24,620); nmr(CDCl$_3$)$\delta$ 2.7(6H,m), 2.9(1H,s), 3.7(2H, t), 4.05(4H,t) and 7.7(5H,m) and Anal. Calcd for $C_{14}H_{18}N_4O$: C, 65.09% H, 7.02% N, 21.69% and Found: C, 64.78% H, 6.84% N, 21.43%; 2-[4-(4-chlorophenyl)-1-piperazinyl]cycloheptimidazole (I: $R^1$ is 4-chlorophenyl) mp 220°–221° C. (crystallized from ethyl acetate); ir(mull)1595, 1556, 1516 and 1495 cm$^{-1}$; uv max(MeOH) 286 ($\epsilon$9,354), 262 ($\epsilon$46,358) and 240 nm($\delta$29,070); nmr-(CDCl$_3$)$\delta$3.30(4H,t), 4.20(4H,t) and 7.5(9H,m) and Anal. Calcd for $C_{18}H_{17}N_4Cl$: C, 66.56;1 % H, 5.27% N, 17.25% and Found C, 66.37% H, 5.37% N, 17.50%; 2-[4-(2-pyridinyl)-1-piperazinyl]cycloheptimidazole (I: $R^1$ is 2-pyridinyl): mp 182°–183° C. (crystallized from ethyl acetate); ir(CHCl$_3$)1595, 1565, 1520 and 1485 cm$^{-1}$; uv max (MeOH) 360($\epsilon$22,105), 297($\epsilon$10,915) and 256 nm($\epsilon$41,780); nmr(CDCl$_3$)$\delta$3.75(4H,m) 4.15(4H,m), 6.65(2H,m) and 7.70(7H,m) and Anal. Calcd. for $C_{17}H_{17}N_5$: C, 69.99% H, 5.84% N, 24.10% and Found: C, 69.63% H, 5.83% N, 24.22%; 2-[4-(2-methylphenyl)-1-piperazinyl]cycloheptimidazole (I: $R^1$ is 2-methylphenyl); mp 179°–181° C. (crystallized from ethyl acetate); ir(CHCl$_3$) 1600, 1565, 1520 and 1493 cm$^{-1}$; uv max(MeOH) 262 ($\epsilon$34,300) and 240 nm($\epsilon$31,860); nmr(CDCl$_3$)$\delta$ 2.42(3H,s), 3.05(4H,t), 4.2(4H,t) and 7.5(9H,m) and Anal. Calcd for $C_{19}H_{20}N_4$: C, 75.00% H, 6.60% N, 18.40% and Found: C, 74.95% H, 6.54% N, 18.57%; 2-[4-(4-methoxyphenyl)-1-piperazinyl]cycloheptimidazole (I: $R^1$ is 4-methoxyphenyl): mp 171°–172° C. (crystallized from ethyl acetate); ir(CHCl$_3$) 1604, 1567, 1530 and 1510 cm$^{-1}$; uv max(MeOH) 292 ($\epsilon$9,465), 263($\epsilon$36,460) and 240 nm($\epsilon$34,630); nmr(CDCl$_3$)$\delta$3.2(4H,t), 3.8(3H,s), 4.18 (4H,t) and 6.9–8.1(9H,m) and Anal. Calcd for $C_{19}H_{20}N_4O$: C, 71.22% H, 6.29% N, 17.48% and Found: C, 71.21% H, 6.27% N, 17.66%; 2-[4-(4-fluorophenyl)-1-piperazinyl]cycloheptimidazole (I: $R^1$ 4-fluorophenyl): mp 201°–203° C. (crystallized from ethyl acetate); ir(CHCl$_3$) 1605, 1565, 1525 and 1510 cm$^{-1}$; uv max(MeOH) 292($\epsilon$8,670), 263($\epsilon$42,170), 257($\epsilon$43,200), 251($\epsilon$40,010) and 249 nm($\epsilon$39,540); nmr(CDCl$_3$)$\delta$3.25(4H,t) 4.20(4H,t) and 7.50(9H,m) and Anal. Calcd for $C_{18}H_{17}N_4$: C, 70.10% H, 5.56% N, 18.17% and Found: C, 69.66% H, 5.43% N, 18.02%; 2-[4-(3-trifluoromethylphenyl)-1-piperazinyl]cycloheptimidazole (I: $R^1$ is 3-trifluoromethylphenyl): mp 214°–215° C. (crystallized from ethyl acetate); Ir(mull) 1600, 1566 and 1520 cm$^{-1}$; uv max(MeOH) 291($\epsilon$8,470) and 260 nm($\epsilon$40,055); nmr(CDCl$_3$)$\delta$3.4(4H,t), 4.23(4H,t) and 7.0–8.15(9H,m) and Anal. Calcd for $C_{19}H_{17}F_3N_4$:

C, 63.60% H, 4.79% H, 4.79% N, ;b 15.65% and Found: C, 63.77% H, 4.63% N, 15.70%; 2-[4-(2-methoxyphenyl)-1-piperazinyl]-cycloheptimidazole (I: $R^1$ is 2-methoxyphenyl): mp 127.5°–128.5° C. (crystallized from ethyl acetate); ir(CHCl$_3$) 1600, 1565, 1522 and ;b 1497 cm$^{-1}$; uv max (MeOH) 262($\epsilon$34,650) and 238 nm($\epsilon$31,710); nmr(CDCl$_3$)$\delta$3.2(4H,t), 3.93(3H,s), 4.25(4H,t) and 6.95–8.1(9H,m) and Anal. Calcd for C$_{19}$H$_{20}$N$_4$O: C, 71.22% H, 6.29% N, 17.48% and Found: C, 70.92% H, 6.27% N, 17.45%; and 2-[4-[α-(4-chlorophenyl)-α-phenylmethyl]-piperazinyl)cycloheptimidazole (I: $R^1$ α-(4-chlorophenyl)-α-phenylmethyl): mp 202°–203° C. (crystallized from ethyl acetate); ir(CHCl$_3$) 1600, 1564, 1520 and 1485 cm$^{-1}$; uv max(MeOH) 291($\epsilon$7,920), 262($\epsilon$30,800) and 234 nm($\epsilon$37,190); nmr(CDCl$_3$)$\delta$2.54 (4H,t), 4.02(4H,t), 4.26(1H,s) and 7.3–8.0(14H,m) and Anal. Calcd for C$_{25}$H$_{23}$ClN$_4$: C, 72.63% H, 5.58% N, 13.49% and Found: C, 72.48% H, 5.51% N, 13.52%.

EXAMPLE 16

2,2-DIMETHYLPROPANOIC ACID, 2-[4-(2-CYCLOHEPTIMIDAZOLYL)-]-PIPERAZINYL]ETHYL ESTER (I: $R^1$ is 2,2-DIMETHYLPROPANOIC ACID,

A solution of 4-(2-cycloheptimidazolyl)-1-piperazineethanol (5.16 g, described in Example 15), 2,2;1-dimethylpropionyl chloride (2.64 g) and triethylamine (2.22 g) in methylene chloride (100 ml) was stirred at room temperature for 16 hr and diluted with methylene chloride. The solution was washed with water, dried and evaporated. The residue was crystallized from diethyl ether-hexane to obtain the title compound (2.5 g): mp 92°–93° C; ir(CHCl$_3$) 1725 cm$^{-1}$; uv max(MeOH) 292 ($\epsilon$7,300), 262($\epsilon$27,815) and 238 nm($\epsilon$24,150); nmr(CDCl$_3$)$\delta$1.25(9H,s), 2.65(6H,m), 4.00(4H,t), 4.2(2H,t) and 7.6(5H,m) and Anal. Calcd for C$_{19}$H$_{26}$N$_4$O$_2$: C, 66.64% H, 7.65% N, 16.36% and Found: C, 66.50% H, 7.73% N, 16.36%. We claim:

1. A compound formula I

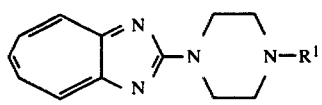

in which $R^1$ is hydrogen, lower alkyl, lower alkenyl, lower alkynyl, hydroxy(lower)-alkyl, lower alkoxycarbonyl, formyl, phenyl(lower)alkyl, phenylcarbonyl, 2- or 3-furanylcarbonyl, phenyl, 2-or 3-pyridinyl, 1-oxo(-lower)alkoxy(lower)alkyl, 2-imidazolinyl, aminoiminomethyl, aminothioxomethyl, (lower alkylamino)thioxomethyl, (phenylamino)thioxomethyl, hydrazinothioxomethyl, (lower alkylthio)thioxomethyl, sodium thiothioxomethyl, α-halophenyl-α-phenylmethyl or phenyl substituted with one or two members selected from the group consisting of halo, lower alkyl, lower alkoxy or trifluoromethyl; or a therapeutically acceptable acid addition salt thereof.

2. The compound of claim 1 in which $R^1$ is hydrogen, lower alkyl, lower alkenyl, lower alkynyl, hydroxy(-lower)alkyl, lower alkoxycarbonyl, formyl, phenyl-(lower)alkyl, phenylcarbonyl, 2-furanylcarbonyl, phenyl, 2-pyridinyl, 1-oxo(lower)-alkoxy(lower)alkyl, 2-imidazolinyl, aminoiminomethyl, aminothioxomethyl, (lower alkylamino)thioxomethyl, (phenylamino)thioxomethyl, hydrazinothioxomethyl, (lower alkylthio)thioxomethyl, sodium thiothioxomethyl, α-halophenyl-α-phenylmethyl or phenyl substituted with one member selected from the group consisting of halo, lower alkyl, lower alkoxy or trifluoromethyl; or a therapeutically acceptable acid addition salt thereof.

3. The compound of claim 1 in which $R^1$ is hydrogen, lower alkyl, lower alkenyl, lower alkynyl, hydroxy(lower)alkyl, lower alkoxycarbonyl, formyl, 2-furanylcarbonyl, 1-oxo(lower)alkoxy(lower)alkyl, aminoiminomethyl, hydrazinothioxomethyl or sodium thiothioxomethy; or a therapeutically acceptable acid addition salt thereof.

4. 4-(2-Cycloheptimidazolyl)-piperazine-1-carboxylic acid ethyl ester; a compound of claim 1 wherein $R^1$ is ethoxycarbonyl.

5. 2-(1-Piperazinyl)cycloheptimidazole, a compound of claim 1 wherein $R^1$ is hydrogen.

6. 4-(2-Cycloheptimidazolyl)-1-piperazinecarboximidamide, a compound of claim 1 wherein $R^1$ is aminoiminomethyl.

7. 2-[4-(2-Imidazolinyl)-1-piperazinyl]-cycloheptimidazole, a compound of claim 1 wherein $R^1$ is 2-imidazolinyl.

8. 2-(2-cycloheptimidazolyl)-piperazine-1-carboxylic acid, 2-methylpropyl ester, a compound of Claim 1 wherein $R^1$ is 2-methylpropoxycarbonyl.

9. 2-[4-(2-Propenyl)-1-piperazinyl]-cycloheptimidazole, a compound of claim 1 wherein $R^1$ is 2-propenyl.

10. 2-[4-(2-Propynyl)-1-piperazinyl]-cycloheptimidazole, a compound of claim 1 wherein $R^1$ is 2-propynyl.

11. 4-(2-Cycloheptimidazolyl)-piperazine-1-carbothioic acid, sodium salt, a compound of claim 1 wherein $R^1$ is sodium thiothioxomethyl.

12. 4-(2-cycloheptimidazolyl)-piperazine-1-carbothioic acid, S-methyl ester, a compound of claim 1 wherein $R^1$ is (methylthio)thioxomethyl.

13. 4-(2-Cycloheptimidazolyl)-piperazine-1-carbothioic acid hydrazide, a compound of claim 1 wherein $R^1$ is hydrazinothioxomethyl.

14. 4-(2-Cycloheptimidazolyl)-piperazine-1-carbothioamide, a compound of claim 1 wherein $R^1$ is aminothioxomethyl.

15. 4-(2-Cycloheptimidazolyl)-N-phenyl-piperazine-1-carbothioamide, a compound of claim 1 wherein $R^1$ is (phenylamino)thioxomethyl.

16. 4-(2-Cycloheptimidazolyl)-N-methyl-piperazine-1-carbothioamide, a compound of claim 1 wherein $R^1$ is (methylamino)thioxomethyl.

17. 2-(4-Methyl-1-piperazinyl)cycloheptimidazole, a compound of claim 1 wherein $R^1$ is methyl.

18. 2-[4-(2-Furanylcarbonyl)-1-piperazinyl]cycloheptimidazole, a compound of claim 1 wherein $R^1$ is 2-furanylcarbonyl.

19. 2-(4-Benzoyl-1-piperazinyl)cycloheptimidazole, a compound of claim 1 wherein $R^1$ is benzoyl.

20. 2-[4-(Phenylmethyl)-1-piperazinyl]cycloheptimidazole, a compound of claim 1 wherein $R^1$ is phenylmethyl.

21. 2-(4-Phenyl-1-piperazinyl)cycloheptimidazole, a compound of claim 1 wherein $R^1$ is phenyl.

22. 2-(4-Formyl-1-piperazinyl)cycloheptimidazole, a compound of claim 1 wherein $R^1$ is formyl.

23. 2-[4-(3-Chlorophenyl)-1-piperazinyl]cycloheptimidazole, a compound of claim 1 wherein $R^1$ is 3-chlorophenyl.

24. 4-(2-Cycloheptimidazolyl)-1-piperazineethanol, a compound of claim 1 wherein $R^1$ is 2-hydroxyethyl.

25. 2-[4-(4-Chlorophenyl)-1-piperazinyl]cycloheptimidazole, a compound of claim 1 wherein $R^1$ is 4-chlorophenyl.

26. 2-[4-(2-Pyridinyl)-1-piperazinyl]cycloheptimidazole, a compound of claim 1 wherein $R^1$ is 2-pyridinyl.

27. 2-[4-(2-Methylphenyl)-1-piperazinyl]cycloheptimidazole, a compound of claim 1 wherein $R^1$ is 2-methylphenyl.

28. 2-[4-(4-Methoxyphenyl)-1-piperazinyl]cycloheptimidazole, a compound of claim 1 wherein $R^1$ is 4-methoxyphenyl.

29. 2-[4-(4-Fluorophenyl)1-piperazinyl]cycloheptimidazole, a compound of claim 1 wherein $R^1$ is 4-fluorophenyl.

30. 2-[4-(3-Trifluoromethylphenyl)-1-piperazinyl]cycloheptimidazole, a compound of claim 1 wherein $R^1$ is 3-trifluoromethylphenyl.

31. 2-[4-(2-Methoxyphenyl)-1-piperazinyl]cycloheptimidazole, a compound of claim 1 wherein $R^1$ is 2-methoxyphenyl.

32. 2-[4-[α-(4-Chlorophenyl)-α-phenylmethyl]-1-piperazinyl]cycloheptimidazole, a compound of claim 1 wherein $R^1$ is α-(4-chlorophenyl)-α-phenylmethyl.

33. 2,2-Dimethylpropanoic acid, 2-[4-(2-cycloheptimidazolyl)-1-piperazinyl]ethyl ester, a compound of claim 1 wherein $R^1$ is 2-(2,2-dimethyl-1-oxo-propoxy)ethyl.

* * * * *